US 6,355,063 B1

(12) United States Patent
Calcote

(10) Patent No.: US 6,355,063 B1
(45) Date of Patent: Mar. 12, 2002

(54) EXPANDED PTFE DRUG DELIVERY GRAFT

(75) Inventor: Robert W. Calcote, Phoenix, AZ (US)

(73) Assignee: Impra, Inc., Tempe, AZ (US)

( * ) Notice: Subject to any disclaimer, the term of this patent is extended or adjusted under 35 U.S.C. 154(b) by 0 days.

(21) Appl. No.: 09/488,625

(22) Filed: Jan. 20, 2000

(51) Int. Cl.$^7$ ................................................ A61F 2/06
(52) U.S. Cl. ................................................ 623/1.42
(58) Field of Search ........................ 623/1.39, 1.42, 623/1.4, 1.27, 1.32, 1.22, 1.33, 1.25, 1.43

(56) References Cited

U.S. PATENT DOCUMENTS

| | | |
|---|---|---|
| 3,797,485 A | 3/1974 | Urquhart |
| RE31,618 E | 7/1984 | Mano et al. |
| 5,156,620 A | 10/1992 | Pigott |
| 5,192,310 A | 3/1993 | Herweck et al. |
| 5,197,976 A | 3/1993 | Herweck et al. |
| 5,399,352 A | 3/1995 | Hanson |
| 5,411,550 A | 5/1995 | Herweck et al. |
| 5,556,426 A | 9/1996 | Popadiuk et al. |
| 5,607,478 A | 3/1997 | Lentz et al. |
| 5,609,624 A * | 3/1997 | Kalis ........................ 623/1.32 |
| 5,716,395 A | 2/1998 | Myers et al. |
| 5,716,660 A | 2/1998 | Weadock et al. |
| 5,735,897 A | 4/1998 | Buirge |
| 5,795,318 A | 8/1998 | Wang et al. |
| 5,800,512 A | 9/1998 | Lentz et al. |
| 5,827,327 A | 10/1998 | McHaney et al. |
| 5,833,651 A | 11/1998 | Donovan et al. |
| 5,849,036 A | 12/1998 | Zarate |
| 5,851,230 A | 12/1998 | Weadock et al. |
| 5,865,723 A | 2/1999 | Love |
| 5,871,537 A * | 2/1999 | Holman et al. ............. 623/1.25 |
| 5,891,108 A * | 4/1999 | Leone et al. ................ 623/264 |
| 5,951,458 A | 9/1999 | Hastings et al. |
| 5,976,192 A * | 11/1999 | McIntyre et al. ........... 623/901 |
| 6,053,943 A * | 4/2000 | Edwin et al. ............... 623/1.25 |
| 6,071,305 A * | 6/2000 | Brown et al. ............... 623/1.43 |
| 6,080,198 A * | 6/2000 | Lentz et al. ................ 623/901 |
| 6,162,244 A * | 12/2000 | Braun et al. ............... 623/1.12 |
| 6,214,042 B1 * | 4/2001 | Jacobsen et al. ............ 623/1.2 |

FOREIGN PATENT DOCUMENTS

| | | |
|---|---|---|
| WO | WO 93/05730 A1 | 4/1993 |
| WO | WO 98/23228 A1 | 6/1998 |
| WO | WO 00/18331 A2 | 4/2000 |
| WO | PCT/US 01/02061 | 6/2001 |

OTHER PUBLICATIONS

"Directions for Use" for XP–000945424, IMPRA, 1988 (whole document).

* cited by examiner

Primary Examiner—David H. Willse
Assistant Examiner—Suzette J. Jackson
(74) Attorney, Agent, or Firm—Todd W. Wight; Morrison & Foerster

(57) ABSTRACT

An improved ePTFE-based delivery graft is intended to dispense a bioactive agent such as a drug into the blood stream. A hollow tubing is infused with the agent from a source such as a drug delivery pump mechanism. The spiral hollow tubing is wrapped in a helical fashion around, or otherwise brought into contact with an outer wall of a porous ePTFE graft and adhered thereto. The agent is delivered to the lumen of the graft by infusing the agent through the porous interstices of the graft wall. Thus, the bioactive agent is conducted by the hollow tubing from a source to the outer surface of an ePTFE graft where it is released to diffuse into the graft to influence biological processes along both the inner and outer surfaces of the graft. The present invention allows the bioactive agent or drug to be renewed or changed after implant of the graft. In addition the present invention can be implanted in the same fashion as regular vascular grafts.

25 Claims, 3 Drawing Sheets

EXPANDED PTFE DRUG DELIVERY GRAFT

BACKGROUND OF THE INVENTION

1. Field of the Invention

The present invention relates to medical devices, and more particularly, to an expanded polytetrafluoroethylene (ePTFE) based graft for delivering an agent into a natural tissue conduit, e.g., a blood vessel.

2. Description of Related Art

Providing frequent, direct delivery of bioactive agents to a natural tissue conduit has become a necessity for many medical treatments such as those requiring frequent intravenous administration of drugs. To meet this need, many types of devices including stents and vascular grafts have been used to deliver agents into natural tissue conduits.

Local delivery is advantageous in that the effective local concentration of a delivered drug can be much higher than can normally be achieved by systemic administration. Delivery of agents to vascular tissue to prevent restenosis is especially useful. U.S. Pat. No. 5,399,352 to Hanson discloses a device for delivering an effective concentration of a therapeutic agent locally at a target site within the body without producing unwanted systemic side effects. However, the device described in this reference differs considerably from existing vascular grafts. It would be especially advantageous to deliver drugs with a device more similar to currently used vascular grafts.

Stents and other existing devices are frequently coated with or impregnated with therapeutic agents for the treatment of diseases. A concern related to the use of stents and existing devices for drug delivery is that drug delivery may not be sustainable. Over time the concentration of drug on the stent or other similar delivery devices will diminish, through drug inactivation, degradation, or dilution. Thus, the therapeutic agent may need to be refreshed or even changed after implant of the device. Moreover, these existing devices are not capable of delivering drugs to an internal lumen along the entire length of the graft.

Accordingly, it would be desirable to provide a drug delivery graft capable of delivering a drug or any other agent to the internal lumen along the entire length of the graft, or restrict delivery to a finite area on the graft such that the agent may be renewed or altered after implant of the graft. Furthermore, a desirable drug delivery graft could be implanted in the same fashion as regular vascular grafts.

SUMMARY OF THE INVENTION

In accordance with the teachings of the present invention, an improved expanded polytetrafluoroethylene (ePTFE) drug delivery graft is provided. The invention can be used, for example, as a vascular graft providing sustained release of a selected bioactive or diagnostic agent directly into a blood or other fluid flow pathway. The graft is capable of delivering the bioactive or diagnostic agent to the internal lumen of a vascular graft along the entire length, or of restricting delivery to a finite area of the vascular graft. Various ePTFE grafts that are reinforced by external beading are well known in the art. However, unlike previous designs that utilize a solid beading for reinforcing purposes, the present design utilizes a hollow tubing as a drug conduit. Also, the hollow tubing behaves much like the existing low profile solid beading in that it has a small diameter and can be readily implanted into the body. The hollow tubing of the present invention serves as both a spiral support and drug conduit.

A simple tubular ePTFE graft is used, which is well known to be extremely porous. A hollow tubing of non-porous PTFE, fluoroethylene polymer (FEP) or other implantable polymer is wrapped around the graft and laminated or adhered in place. The hollow tubing may be wrapped helically; alternatively other arrangements (e.g., end to end loops) can be used. Before the wrapping occurs one surface of the hollow tubing is cut away (for example, laser cut), punctured repeatedly or otherwise rendered porous. When an agent such as a drug is injected into the hollow tubing, e.g., from an infusion pump or a subcutaneous access port, the drug flows through the hollow tubing and leaks through the cut or porous region and diffuses into the outer surface of the ePTFE graft. The drug diffuses into the graft where it mixes into the blood flowing therethrough and influences biological processes along the circulatory system. Depending on the drug used and the precise configuration of the device the dispensed material could have either systemic effect or have limited local effect. One particularly attractive use of the device is to dispense drugs to limit the restenosis that frequently occurs due to tissue proliferation at the site of anastimosis of an ePTFE graft to a blood vessel.

The invention takes advantage of the well-known porosity of an ePTFE graft. Impregnation of ePTFE grafts with therapeutic agents has been previously disclosed. However, the present invention allows the therapeutic agents to be renewed or altered following implant of the graft, something that is not possible with simple drug-impregnated graft materials.

A more complete understanding of the ePTFE drug delivery graft will be afforded to those skilled in the art, as well as a realization of additional advantages and objects thereof, by a consideration of the following detailed description of the preferred embodiment. Reference will be made to the appended sheets of drawings that will first be described briefly.

DETAILED DESCRIPTION OF THE PREFERRED EMBODIMENT

Figure 1:
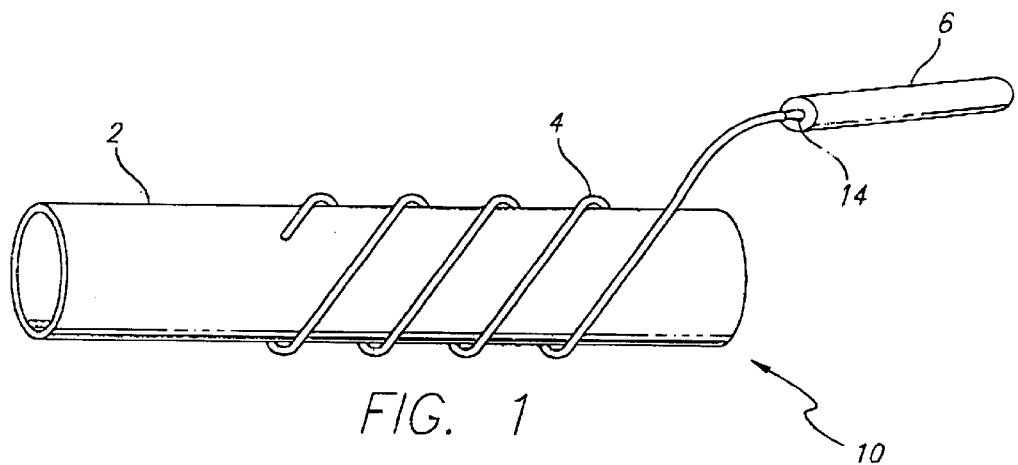
FIG. 1 is a side view of a drug delivery graft according to an embodiment of the present invention.

The present invention satisfies the need for an improved drug delivery graft capable of delivering bioactive agents, including drugs, to an internal lumen of a graft, either along its entire length or in a localized area, through the use of hollow tubing on the outside of the graft. In the detailed description that follows, it should be appreciated that like reference numerals are used to identify like elements illustrated in one or more of the figures.

Referring first to FIG. 1, a side view of a drug delivery graft 10 in accordance with an embodiment of the present invention is illustrated. The drug delivery graft 10 comprises a graft 2, a hollow tubing 4, and a drug source 6. The hollow tubing 4 is wrapped (spiraled) in a helical fashion around an abluminal surface of the graft 2. The drug source 6 is connected to one end 14 of the hollow tubing 4.

The graft 2 may be a standard clinical vascular graft of any shape or size comprised preferably of expanded PTFE, which material consists of a porous network of nodes and fibrils created during the expansion process. This porous network provides a somewhat permeable wall for the graft 2. The graft 2 can be constructed in a variety of sizes to allow a surgeon to select the appropriate size to accommodate a particular vascular application. Likewise, the porosity (internodal distance) of the graft can be varied to affect the rate of drug or agent release.

The drug delivery graft 10 injects a drug or other agent into the bore of the hollow tubing 4 from the drug source 6. The drug source 6 can be any of a variety of commercially and technologically available systems that provide constant controlled rate delivery of an agent, such as a biologically activated mini pump that is either subcutaneously or extracorporeally located, an external mechanical pump, or an access port. For example, an open end 14 of the hollow tubing 4 may be connected via a micro-catheter to a subcutaneous or other drug source.

The agent delivered to the natural tissue conduit can be any substance, including any drug, and the device can be used for local or systemic delivery of such substances to prevent or treat a variety of disease syndromes or to promote or enhance desired activity within the body. A bioactive or diagnostic agent may include, for example, therapeutic or prophylactic agents, such as a drug, protein, enzyme, antibody or other agent, or cells that produce a drug, protein, enzyme, antibody, or other agent. The diagnostic material can include, for example, a radiolabeled antibody or antigen.

The natural tissue conduit into which the agent is ultimately delivered may include any structure of a body that functions to transport substances and includes, but is not limited to, e.g., blood vessels of the cardiovascular system (arteries and veins), the lymphatic system, the intestinal tract (esophagus, stomach, the small and large intestines, and colon), the portal system of the liver, the gall bladder and bile duct, the urinary system (bladder, and urethra), the respiratory system (trachea, bronchi and bronchioles), and ducts and ductules connecting endocrine organs to other areas of the body. The device of the present invention can be used in any mammal or in any animal in which natural tissue conduits are found. Suitable dosage requirements and treatment regimens for any agent delivered can be determined and will vary depending upon the tissue targeted for therapy and upon the particular agent utilized.

Figure 2:
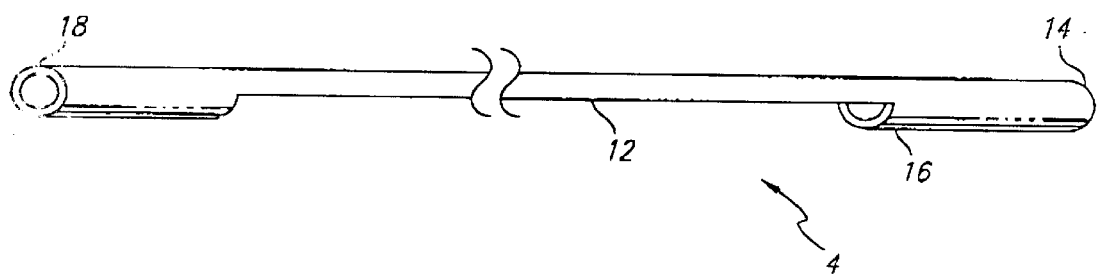
FIG. 2 is a side view of a hollow tubing according to an embodiment of the present invention.

Referring now to FIG. 2, a side view of the hollow tubing 4 used in an embodiment of the present invention is illustrated. The hollow tubing 4 may be manufactured from a non-expanded or partially expanded small diameter PTFE tube or any other implantable polymer (e.g. FEP). The hollow tubing 4 may be manufactured in very small diameters (less than 1 mm) and long lengths (more than 10 feet) to accommodate all sizes of grafts. Whereas the prior art beading used solely for support purposes is a solid filament, the hollow tubing 4 has a bore to provide fluid delivery to the graft 2. Preferably, the hollow tubing 4 has an uncut portion 16 and a partially cut portion 12 (or a porous and less or non-porous region arrange circumferentially) that allows communication between the lumen of the hollow tubing 4 and the outside surface of the graft 2. Alternatively, communication between the lumen of the hollow tubing 4 and the outside surface of the graft 2 may be achieved by using a porous hollow tubing or a hollow tubing with mechanical or laser perforations. While the hollow tubing 4, is shown generally cylindrical in shape, it should be appreciated that alternative designs are possible including a hollow tubing that is tapered along its length as well as one that has a stepped configuration or has other, non-circular cross-sections. Similarly the graft may be tapered or stepped or of a special shape, such as cuffed, as is known in the art.

In a preferred embodiment, to manufacture the hollow tubing 4, a specified length of a tube made of PTFE, FEP or other any other implantable polymer may be loaded on a mandrel to secure the tube in a rigid fashion. The loaded tube may be placed in a cutting device where a defined portion of the tube is cut in the longitudinal direction. A semi-circular "half-tube" C-shaped section 12 may be created in the middle of the tube to create the hollow tubing 4. The cutting device may comprise a LASER cutting device. Alternatively, the tube may be punctured repeatedly or otherwise rendered porous to allow release of the agent into the ePTFE of the graft. One end 18 of the hollow tubing 4 may be sealed mechanically, for example by a crimp, or by a heating process to terminate the lumen. The terminated end 18 may also be sealed with a silicon or other self-sealing material that can advantageously serve as a primer port for infusing an agent through, for example, a syringe.

Figure 3:
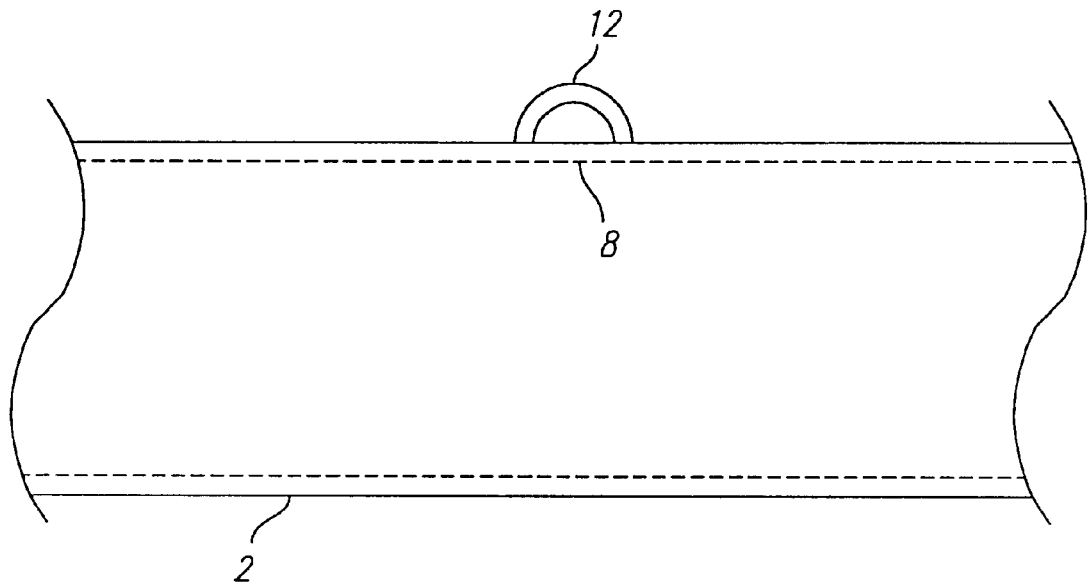
FIG. 3 is a cross-sectional view of the drug delivery graft showing a cut portion of the hollow tubing according to an embodiment of the present invention.
Figure 4:
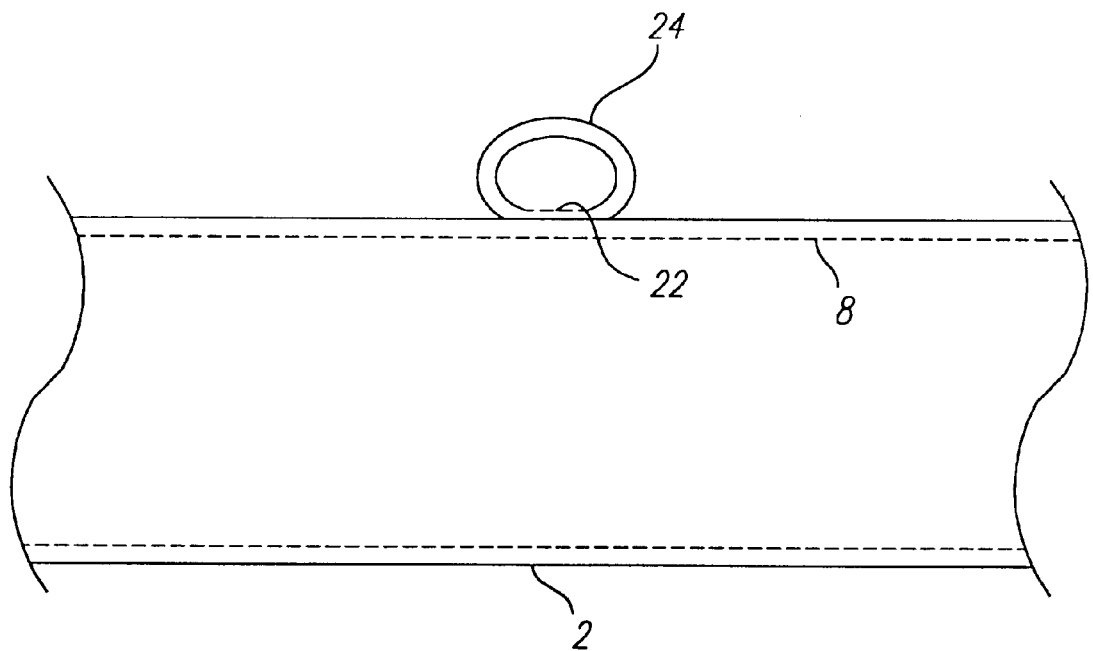
FIG. 4 is a cross-sectional view of the drug delivery graft showing a porous hollow tubing according to an embodiment of the present invention.

Referring now to FIG. 3, a cross-sectional view of the drug delivery graft showing a cut portion of hollow tubing according to an embodiment of the present invention is illustrated. Hollow tubing 4 is wound spirally around the graft 2. During the spiraling process, a cutaway portion 12 of the hollow tubing 4 is laminated and secured against the outer surface of the graft 2, creating a drug outflow surface that communicates with the outer lumen of the graft 2. Alternatively, FIG. 4 shows a cross-sectional view of the drug delivery graft showing a porous hollow tubing 24 according to an alternative embodiment of the present invention. The porous hollow tubing 24 comprises perforations or pores 22 through which an agent or drug is dispensed onto and into the graft 2. The agent or drug is evenly distributed and diffuses into the graft 2 through the interstices of an agent infusion area 8. The rate at which the drug or other agent penetrates the porous wall of the graft 2 is determined by several factors, including the size and number of the pores and the size of the drug molecule. The graft 2 is capable of delivering drugs or any other agents to the internal lumen along the entire length of the graft 2, or of restricting delivery to a finite area on the graft 2. In addition, it should be appreciated that the spacing of the hollow tubing 4 along the graft 2 can be varied to concentrate dosages in certain areas of need. Moreover, the spiraling of the hollow tubing 4 around the graft 2, as shown in FIG. 1, could be combined with a traditional support beading spiraled around the graft 2 for additional support.

Figure 5:
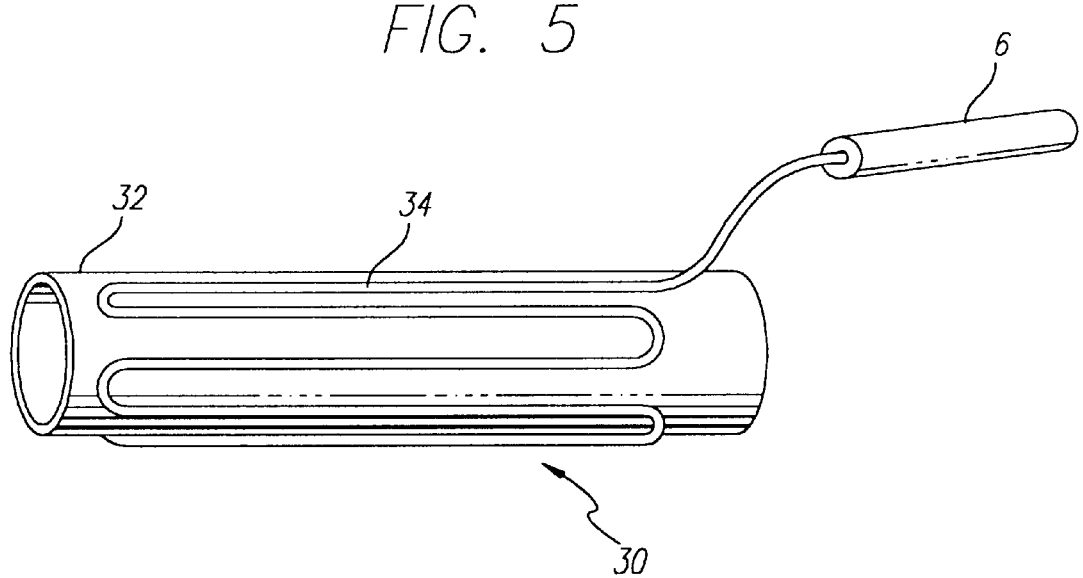
FIG. 5 is a side view of an alternate embodiment of the drug delivery graft of the present invention.
Figure 6:
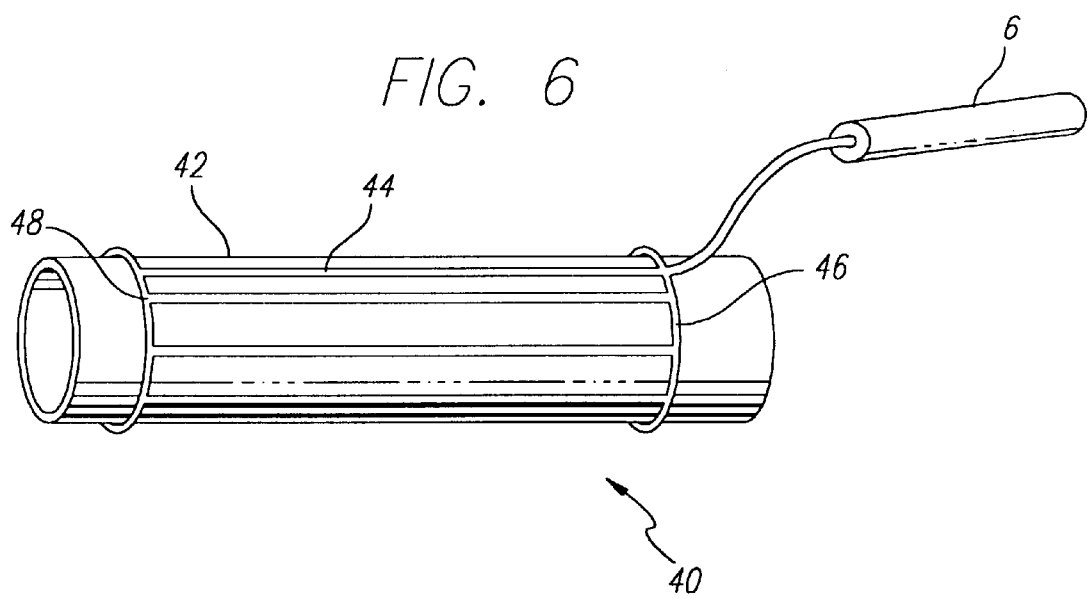
FIG. 6 is a side view of another alternate embodiment of the drug delivery graft of the present invention.

Turning now to FIG. 5, an alternate embodiment of the present invention is shown. Drug delivery graft 30 includes graft 32 and hollow tubing 34. In this embodiment, the hollow tubing 34 is arranged longitudinally along the graft 32, rather than wrapped around spirally as in FIG. 1. The hollow tubing 34 is arranged in snake-like fashion, longitudinally along the outside of the graft 32, and is connected to the drug source 6 at one end. The longitudinally arranged strips of hollow tubing 34 loop back at the ends of the graft so that a single continuous piece of hollow tubing is employed. In a second alternate embodiment illustrated in FIG. 6, hollow tubing 44 is arranged longitudinally along a graft 42 in a slightly different configuration to make up a drug delivery graft 40. In this embodiment, the longitudinally arranged hollow tubing 44 is connected to manifolds 46 and 48 at each end. The manifold 46, located at a proximal end of the graft 42, is circumferentially arranged around the graft 42 and is also connected to the drug source 6. The manifold 48, located at a distal end of the graft 42 is cirumferentially arranged around the graft 42 in a closed loop. The drug provided from the drug source 6 flows into the manifold 46 where it is distributed to the longitudinally placed hollow tubing 44, flowing through the hollow tubing 44 and along the manifold 48, being distributed to the graft 42 in one of the above-mentioned methods shown in FIGS. 2–4. It should be appreciated that in both embodiments shown in FIGS. 5 and 6, the hollow tubing can be spaced equidistant or varied depending on the required application.

The spiraled or longitudinally-placed hollow tubing is sintered to the graft to adhere the hollow tubing to the graft in the same manner as existing standard grafts, adhering the cut (C-shaped) portion 12 and uncut hollow tubing portion 16 as shown in FIG. 3, or the porous hollow tubing 24 as shown in FIG. 4, along the length of the graft 2. Alternatively, any of a number of known adhesive agents can be used to attach the hollow tubing. Further, the hollow tubing may be produced from a plastic material such as polypropylene, which can be adhered to the graft through a partial melting process. Thus, the design may use the existing low profile hollow tubing on existing grafts, for example IMPRAFlex® grafts, manufactured by IMPRA (Tempe, Ariz.), a Division of C.R. Bard, Inc., and can be implanted in the same fashion as regularly used existing vascular grafts.

The devices of the present invention can function as improved vascular grafts such that the agent or drug to be delivered prevents or treats complications associated with conventional vascular graft placement, including but not limited to platelet deposition, coagulation, thrombosis, neointimal hyperplasia and fibrosis. One particularly attractive use of the drug delivery graft would be to dispense drugs or any other agent to limit the stenosis that frequently occurs at the site of anastimosis of an ePTFE graft to a blood vessel. Examples of agents that prevent restenosis of a blood vessel include, but are not limited to, a growth factor, a growth factor inhibitor, growth factor receptor antagonist, transcriptional repressor, translational repressor, antisense DNA, antisense RNA, replication inhibitor, anti-microtubule agents, inhibitory antibodies, antibodies directed against growth factors or their receptors, bifunctional molecules comprising a growth factor and a cytotoxin, and bifunctional molecules comprising an antibody and a cytotoxin.

Having thus described a preferred embodiment of the expanded PTFE drug delivery graft, it should be apparent to those skilled in the art that certain advantages of the within system have been achieved. It should also be appreciated that various modifications, adaptations, and alternative embodiments thereof may be made within the scope and spirit of the present invention. The invention is further defined by the following claims.

What is claimed is:

1. A drug delivery graft comprising:

a graft having a lumen and a porous wall; and a hollow tubing having a bore, running along an exterior surface of said graft in fluid communication with said porous wall of said graft, wherein a drug is infused into said bore of said hollow tubing to penetrate into said lumen of said graft through said porous wall.

2. The drug delivery graft of claim 1 further comprising a drug source attached to one end of said hollow tubing.

3. The drug delivery graft of claim 1, wherein said hollow tube is wrapped helically around the outer surface of said graft.

4. The drug delivery graft of claim 1, wherein said hollow tube is arranged substantially parallel to a longitudinal axis of said graft.

5. The drug delivery graft of claim 1, wherein said graft comprises ePTFE.

6. The drug delivery graft of claim 1, wherein said hollow tubing comprises a cutaway portion in contact with said porous wall of said graft.

7. The drug delivery graft of claim 1, wherein said hollow tubing comprises perforations communicating said bore of said hollow tubing with said porous wall of said graft.

8. The drug delivery graft of claim 1, wherein said hollow tubing comprises a porous wall allowing fluid communication with said porous wall of said graft.

9. The drug delivery graft of claim 2, wherein said drug source further comprises a drug delivery pump.

10. The drug delivery graft of claim 2, wherein said drug is selected to prevent restenosis of a blood vessel.

11. The drug delivery graft of claim 10, wherein said drug is selected from the group consisting of a growth factor, a growth factor inhibitor, growth factor receptor antagonist, a transcriptional repressor, a translational repressor, an antisense nucleic acid, a replication inhibitor, an anti-microtubule agent, an inhibitory antibody, an antibody directed against a growth factor, a bifunctional molecules comprising a growth factor and a cytotoxin, and a bifunctional molecule comprising an antibody and a cytotoxin.

12. A drug delivery device comprising:

porous graft means for replacing a natural tissue conduit; and hollow tubing means in contact with an outer surface of said porous graft means for delivering a drug to said porous graft means via areas in contact with said porous graft means.

13. The drug delivery device of claim 12, wherein the hollow tubing means is wrapped helically about said porous graft means.

14. The drug delivery device of claim 12 further comprising drug infusing means for infusing said drug into said hollow tubing means.

15. The drug delivery device of claim 12, wherein said areas in communication with said porous graft means comprise a cutaway section.

16. The drug delivery device of claim 12, wherein said areas in communication with said porous graft means comprise perforations on said hollow tubing means.

17. The drug delivery device of claim 12, wherein said areas in communication with said porous graft means comprise a porous region on said hollow tubing means.

18. A drug delivery system manufactured by a process comprising the steps of:

providing a porous graft;

providing a small diameter hollow tubing having defined porous areas;

bringing said small diameter hollow tubing into contact with said porous graft such that said defined porous areas are secured against an outer surface of the porous graft; and connecting an end of the small diameter beading to a drug source so that a drug from the drug source enters said small diameter hollow tubing and passes through the porous areas into said porous graft.

19. The drug delivery system of claim 18, wherein said small diameter hollow tubing is wrapped helically about said porous graft.

20. The drug delivery system of claim 18, wherein said defined porous areas of said small diameter hollow tubing comprise cut away sections of said small diameter hollow tubing.

21. The drug delivery system of claim 18, wherein said process further comprises the step of using a cutting device to cut said defined porous areas into said small diameter hollow tubing.

22. The drug delivery system of claim 18, wherein said defined porous areas of said small diameter hollow tubing further comprise perforations on said small diameter hollow tubing.

23. The drug delivery system of claim 18, wherein said connecting step further comprises connecting said unsealed end of said small diameter hollow tubing to a drug infusion pump.

24. A method of preventing restenosis of a blood vessel comprising the steps of:

providing a porous graft;

providing a small diameter hollow tubing in contact with said graft and having a porous region in fluid communication with an outer surface of said porous graft;

connecting an end of said small diameter hollow tubing to an anti-restenosis agent source;

delivering said anti-restenosis agent to said blood vessel via said small diameter hollow tubing and said porous graft.

25. The method of claim 24, wherein said anti-restenosis agent is selected from the group consisting of a growth factor, a growth factor inhibitor, growth factor receptor antagonist, a transcriptional repressor, a translational repressor, an antisense nucleic acid, a replication inhibitor, an anti-microtubule agent, an inhibitory antibody, an antibody directed against a growth factor, a bifunctional molecules comprising a growth factor and a cytotoxin, and a bifunctional molecule comprising an antibody and a cytotoxin.

* * * * *